(12) United States Patent
Page et al.

(10) Patent No.: US 8,425,555 B2
(45) Date of Patent: Apr. 23, 2013

(54) SUTURE LOCK FASTENING DEVICE

(75) Inventors: Edward C. Page, Baldwinville, MA (US); Patrick Gutelius, Monroe, CT (US); Danial P. Ferreira, Milford, CT (US); Jeffrey P. Radziunas, Wallingford, CT (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 13/330,023

(22) Filed: Dec. 19, 2011

(65) Prior Publication Data
US 2012/0089182 A1 Apr. 12, 2012

Related U.S. Application Data

(63) Continuation of application No. 11/436,398, filed on May 18, 2006, now Pat. No. 8,105,355.

(51) Int. Cl.
*A61B 17/04* (2006.01)

(52) U.S. Cl.
USPC .......................................................... 606/232

(58) Field of Classification Search .......................... None
See application file for complete search history.

(56) References Cited

U.S. PATENT DOCUMENTS

| | | | |
|---|---|---|---|
| 4,379,358 A * | 4/1983 | Wibrow | 24/136 R |
| 4,455,717 A * | 6/1984 | Gray | 24/115 R |
| 5,037,433 A | 8/1991 | Wilk et al. | |
| 5,116,349 A | 5/1992 | Aranyi | |
| 5,217,472 A | 6/1993 | Green et al. | |
| 5,224,948 A | 7/1993 | Abe et al. | |
| 5,364,407 A | 11/1994 | Poll | |
| 5,383,905 A | 1/1995 | Golds et al. | |
| 5,405,351 A | 4/1995 | Kinet et al. | |
| 5,405,354 A | 4/1995 | Sarrett | |
| 5,411,523 A * | 5/1995 | Goble | 606/232 |
| 5,439,467 A | 8/1995 | Benderev et al. | |

(Continued)

FOREIGN PATENT DOCUMENTS

| | | |
|---|---|---|
| WO | WO 93/08747 A1 | 5/1993 |
| WO | WO 99/04699 A1 | 2/1999 |

(Continued)

OTHER PUBLICATIONS

Extended Search Report of the European Patent Office for European Application No. EP 11180293.0, dated Nov. 18, 2011 (6 pages).

(Continued)

*Primary Examiner* — Melanie Tyson
*Assistant Examiner* — Son Dang
(74) *Attorney, Agent, or Firm* — Wolf, Greenfield & Sacks, P.C.

(57) ABSTRACT

A suture lock fastening device to cinch a suture in a suture lock, cut the suture end, and deploy the suture lock in response to a single movement of a user. The fastening device includes a fastening head with a retainer that is configured to hold a suture lock in the fastening head. To release the suture lock from the fastening head, the retainer is irreversibly deformed. The fastening device may include an axially movable cutter with a cutting edge to sever the ends of the suture close to the suture lock. A threading device may be preloaded into the fastening device to facilitate threading the suture through the fastening device.

25 Claims, 9 Drawing Sheets

U.S. PATENT DOCUMENTS

| | | | |
|---|---|---|---|
| 5,462,558 A | 10/1995 | Kolesa et al. | |
| 5,501,692 A | 3/1996 | Riza | |
| 5,520,702 A | 5/1996 | Sauer et al. | |
| 5,536,273 A | 7/1996 | Lehrer | |
| 5,544,664 A | 8/1996 | Benderev et al. | |
| 5,545,180 A | 8/1996 | Le et al. | |
| 5,582,188 A | 12/1996 | Benderev et al. | |
| 5,591,177 A | 1/1997 | Lehrer | |
| 5,593,425 A * | 1/1997 | Bonutti et al. | 606/232 |
| 5,609,597 A | 3/1997 | Lehrer | |
| 5,611,515 A | 3/1997 | Benderev et al. | |
| 5,616,131 A | 4/1997 | Sauer et al. | |
| 5,618,314 A | 4/1997 | Harwin et al. | |
| 5,620,012 A | 4/1997 | Benderev et al. | |
| 5,626,590 A | 5/1997 | Wilk | |
| 5,630,824 A | 5/1997 | Hart | |
| 5,630,825 A | 5/1997 | de la Torre et al. | |
| 5,643,289 A | 7/1997 | Sauer et al. | |
| 5,643,321 A * | 7/1997 | McDevitt | 606/232 |
| 5,645,553 A | 7/1997 | Kolesa et al. | |
| 5,649,963 A * | 7/1997 | McDevitt | 606/232 |
| 5,665,109 A | 9/1997 | Yoon | |
| 5,669,917 A | 9/1997 | Sauer et al. | |
| 5,718,717 A | 2/1998 | Bonutti | |
| 5,725,529 A * | 3/1998 | Nicholson et al. | 606/232 |
| 5,741,301 A | 4/1998 | Pagedas | |
| 5,746,763 A | 5/1998 | Benderev et al. | |
| 5,749,884 A | 5/1998 | Benderev et al. | |
| 5,766,221 A | 6/1998 | Benderev et al. | |
| 5,813,408 A | 9/1998 | Benderev et al. | |
| 5,817,111 A | 10/1998 | Riza | |
| 5,827,306 A | 10/1998 | Yoon | |
| 5,836,314 A | 11/1998 | Benderev et al. | |
| 5,836,315 A | 11/1998 | Benderev et al. | |
| 5,842,478 A | 12/1998 | Benderev et al. | |
| 5,855,586 A | 1/1999 | Habara et al. | |
| 5,860,425 A | 1/1999 | Benderev et al. | |
| 5,860,991 A | 1/1999 | Klein et al. | |
| 5,899,921 A * | 5/1999 | Caspari et al. | 606/232 |
| RE36,289 E | 8/1999 | Le et al. | |
| 5,935,129 A * | 8/1999 | McDevitt et al. | 606/232 |
| 5,935,149 A | 8/1999 | Ek | |
| 5,938,686 A | 8/1999 | Benderev et al. | |
| 5,944,739 A | 8/1999 | Zlock et al. | |
| 5,948,001 A | 9/1999 | Larsen | |
| 5,961,538 A * | 10/1999 | Pedlick et al. | 606/232 |
| 5,980,559 A | 11/1999 | Bonutti | |
| 5,993,459 A | 11/1999 | Larsen et al. | |
| 6,001,104 A | 12/1999 | Benderev et al. | |
| 6,007,567 A | 12/1999 | Bonutti | |
| 6,010,525 A | 1/2000 | Bonutti et al. | |
| 6,056,688 A | 5/2000 | Benderev et al. | |
| 6,077,216 A | 6/2000 | Benderev et al. | |
| 6,086,608 A * | 7/2000 | Ek et al. | 606/232 |
| 6,126,677 A | 10/2000 | Ganaja et al. | |
| 6,152,949 A | 11/2000 | Bonutti | |
| 6,159,234 A | 12/2000 | Bonutti et al. | |
| 6,200,329 B1 | 3/2001 | Fung et al. | |
| 6,231,592 B1 | 5/2001 | Bonutti et al. | |
| 6,306,159 B1 | 10/2001 | Schwartz et al. | |
| 6,332,889 B1 | 12/2001 | Sancoff et al. | |
| 6,368,335 B1 | 4/2002 | Chan | |
| 6,432,123 B2 | 8/2002 | Schwartz et al. | |
| 6,475,230 B1 | 11/2002 | Bonutti et al. | |
| 6,508,829 B1 | 1/2003 | Levinson et al. | |
| 6,511,489 B2 | 1/2003 | Field et al. | |
| 6,524,328 B2 | 2/2003 | Levinson | |
| 6,527,785 B2 | 3/2003 | Sancoff et al. | |
| 6,527,794 B1 * | 3/2003 | McDevitt et al. | 606/232 |
| 6,533,796 B1 | 3/2003 | Sauer et al. | |
| 6,572,635 B1 | 6/2003 | Bonutti | |
| 6,575,987 B2 | 6/2003 | Gellman et al. | |
| 6,629,984 B1 | 10/2003 | Chan | |
| 6,663,643 B2 | 12/2003 | Field et al. | |
| 6,692,516 B2 | 2/2004 | West, Jr. et al. | |
| 6,695,852 B2 | 2/2004 | Gleason | |
| 6,746,457 B2 | 6/2004 | Dana et al. | |
| 6,767,352 B2 | 7/2004 | Field et al. | |
| 6,786,913 B1 | 9/2004 | Sancoff et al. | |
| 6,884,249 B2 | 4/2005 | May et al. | |
| 6,932,826 B2 | 8/2005 | Chan | |
| 6,932,835 B2 | 8/2005 | Bonutti et al. | |
| 6,942,674 B2 | 9/2005 | Belef et al. | |
| 6,942,684 B2 | 9/2005 | Bonutti | |
| 6,955,683 B2 | 10/2005 | Bonutti | |
| 6,972,027 B2 | 12/2005 | Fallin et al. | |
| 6,997,931 B2 | 2/2006 | Sauer et al. | |
| 7,011,668 B2 | 3/2006 | Sancoff et al. | |
| 7,033,379 B2 | 4/2006 | Peterson | |
| 7,033,380 B2 | 4/2006 | Schwartz et al. | |
| 7,037,315 B2 | 5/2006 | Sancoff et al. | |
| 7,037,324 B2 | 5/2006 | Martinek | |
| 7,048,755 B2 | 5/2006 | Bonutti et al. | |
| 7,081,126 B2 | 7/2006 | McDevitt et al. | |
| 7,087,060 B2 | 8/2006 | Clark | |
| 7,090,690 B2 | 8/2006 | Foerster et al. | |
| 7,094,246 B2 | 8/2006 | Anderson et al. | |
| 7,147,652 B2 | 12/2006 | Bonutti et al. | |
| 7,220,266 B2 | 5/2007 | Gambale | |
| 7,235,086 B2 | 6/2007 | Sauer et al. | |
| 2002/0128666 A1 | 9/2002 | Sancoff et al. | |
| 2002/0156344 A1 | 10/2002 | Pasricha et al. | |
| 2003/0032983 A1 | 2/2003 | Bonutti et al. | |
| 2003/0093091 A1 | 5/2003 | Paolitto et al. | |
| 2003/0114863 A1 | 6/2003 | Field et al. | |
| 2003/0144673 A1 | 7/2003 | Onuki et al. | |
| 2003/0158581 A1 | 8/2003 | Levinson | |
| 2003/0167062 A1 * | 9/2003 | Gambale et al. | 606/138 |
| 2003/0171760 A1 | 9/2003 | Gambale | |
| 2003/0171761 A1 | 9/2003 | Sancoff et al. | |
| 2003/0181924 A1 | 9/2003 | Yamamoto et al. | |
| 2003/0204205 A1 * | 10/2003 | Sauer et al. | 606/232 |
| 2004/0002718 A1 | 1/2004 | Trout, III et al. | |
| 2004/0034369 A1 | 2/2004 | Sauer et al. | |
| 2004/0044366 A1 | 3/2004 | Bonutti et al. | |
| 2004/0087979 A1 | 5/2004 | Field et al. | |
| 2004/0092967 A1 | 5/2004 | Sancoff et al. | |
| 2004/0093031 A1 | 5/2004 | Burkhart et al. | |
| 2004/0098050 A1 | 5/2004 | Foerster et al. | |
| 2004/0147941 A1 | 7/2004 | Takemoto et al. | |
| 2004/0230223 A1 | 11/2004 | Bonutti et al. | |
| 2004/0236374 A1 | 11/2004 | Bonutti et al. | |
| 2004/0243178 A1 | 12/2004 | Haut et al. | |
| 2004/0249392 A1 | 12/2004 | Mikkaichi et al. | |
| 2004/0249393 A1 | 12/2004 | Weisel et al. | |
| 2004/0254592 A1 | 12/2004 | DiCarlo et al. | |
| 2005/0033325 A1 | 2/2005 | May et al. | |
| 2005/0043747 A1 | 2/2005 | Field et al. | |
| 2005/0070922 A1 | 3/2005 | Field et al. | |
| 2005/0085832 A1 | 4/2005 | Sancoff et al. | |
| 2005/0085853 A1 | 4/2005 | Forsberg et al. | |
| 2005/0085855 A1 | 4/2005 | Forsberg | |
| 2005/0096699 A1 | 5/2005 | Wixey et al. | |
| 2005/0143762 A1 | 6/2005 | Paraschac | |
| 2005/0149067 A1 | 7/2005 | Takemoto | |
| 2005/0192599 A1 | 9/2005 | Demarais | |
| 2005/0192601 A1 | 9/2005 | Demarais | |
| 2005/0216059 A1 | 9/2005 | Bonutti et al. | |
| 2005/0228504 A1 | 10/2005 | Demarais | |
| 2005/0240227 A1 | 10/2005 | Bonutti | |
| 2005/0251205 A1 | 11/2005 | Ewers et al. | |
| 2005/0251206 A1 | 11/2005 | Maahs et al. | |
| 2005/0251209 A1 | 11/2005 | Saadat et al. | |
| 2005/0251210 A1 | 11/2005 | Westra et al. | |
| 2005/0261708 A1 | 11/2005 | Pasricha et al. | |
| 2005/0261709 A1 | 11/2005 | Sakamoto et al. | |
| 2005/0267534 A1 | 12/2005 | Bonutti et al. | |
| 2005/0277986 A1 | 12/2005 | Foerster et al. | |
| 2005/0283193 A1 | 12/2005 | Tullberg et al. | |
| 2005/0288688 A1 | 12/2005 | Sakamoto et al. | |
| 2006/0004409 A1 | 1/2006 | Nobis et al. | |
| 2006/0004410 A1 | 1/2006 | Nobis et al. | |
| 2006/0047314 A1 | 3/2006 | Green | |
| 2006/0052801 A1 | 3/2006 | Dreyfuss et al. | |
| 2006/0058844 A1 | 3/2006 | White et al. | |
| 2006/0069396 A1 | 3/2006 | Meade et al. | |
| 2006/0069397 A1 | 3/2006 | Nobles et al. | |

| | | |
|---|---|---|
| 2006/0069399 A1 | 3/2006 | Weisel |
| 2006/0106422 A1 | 5/2006 | Del Rio et al. |
| 2006/0122633 A1 | 6/2006 | To et al. |
| 2006/0135996 A1 | 6/2006 | Schwartz et al. |
| 2006/0142784 A1 | 6/2006 | Kontos |
| 2006/0142799 A1 | 6/2006 | Bonutti |
| 2006/0178680 A1 | 8/2006 | Nelson et al. |
| 2006/0178682 A1 | 8/2006 | Boehlke |
| 2006/0259044 A1 | 11/2006 | Onuki et al. |
| 2006/0264977 A1 | 11/2006 | Dana et al. |
| 2006/0265010 A1 | 11/2006 | Paraschac et al. |
| 2007/0005081 A1 | 1/2007 | Findlay, III et al. |
| 2007/0010829 A1 | 1/2007 | Nobles et al. |
| 2007/0021781 A1 | 1/2007 | Jervis et al. |
| 2007/0093858 A1 * | 4/2007 | Gambale et al. ............... 606/142 |
| 2007/0100375 A1 | 5/2007 | Mikkaichi et al. |
| 2007/0100376 A1 | 5/2007 | Mikkaichi et al. |
| 2007/0106308 A1 | 5/2007 | Onuki et al. |
| 2007/0106309 A1 | 5/2007 | Onuki et al. |
| 2007/0106310 A1 | 5/2007 | Goldin et al. |
| 2010/0114163 A1 * | 5/2010 | Martin ......................... 606/232 |

FOREIGN PATENT DOCUMENTS

| | | |
|---|---|---|
| WO | WO 01/66001 A2 | 9/2001 |
| WO | WO 2004/103189 A1 | 12/2004 |
| WO | WO 2005/110241 A1 | 1/2005 |
| WO | WO 2005/112784 A2 | 12/2005 |
| WO | WO 2005/112785 A2 | 12/2005 |
| WO | WO 2006/044837 A2 | 4/2006 |

OTHER PUBLICATIONS

International Search Report and Written Opinion for PCT/US2007/011671.

* cited by examiner

SUTURE LOCK FASTENING DEVICE

RELATED APPLICATIONS

This application is a continuation of U.S. application Ser. No. 11/436,398, filed on May 18, 2006, which is herein incorporated by reference in its entirety.

BACKGROUND OF INVENTION

1. Field of Invention

Aspects of this invention relate to a fastening device used to secure sutures, and more particularly to a fastening device used to fasten a suture lock.

2. Discussion of Related Art

Suture locks are used in surgical procedures to obviate the need for tying knots in a suture. Suture locks may be particularly useful for endoscopic procedures where tying a knot in a suture may be particularly cumbersome.

Fastening devices may be used to deliver and position a suture lock at a desired location of a suture. The fastening device may then be used to cinch or lock the suture with the suture lock. Examples of various suture locks and fastening devices for fastening a suture lock are disclosed in U.S. Pat. No. 5,584,861 and U.S. Patent Application Publications 2003/0167062; 2003/0171760 and 2005/0033319.

SUMMARY OF INVENTION

In one illustrative embodiment of the invention, a suture lock fastening device comprises an actuation handle and a fastening head operatively coupled to the actuation handle. The fastening head includes a body that is constructed and arranged to support a suture lock, and a retainer that is constructed and arranged to retain at least a portion of the suture lock in the body. The retainer is constructed and arranged to be irreversibly deformed to release the suture lock from the fastening head.

In another illustrative embodiment of the invention, a suture lock fastening device is provided for fastening a suture lock. The suture lock includes a suture lock ring and a suture lock plug that is insertable into the suture lock ring. The suture lock fastening device comprises an actuation handle and a fastening head operatively coupled to the actuation handle. The fastening head includes a body that is constructed and arranged to support the suture lock ring and the suture lock plug, and a retainer that is constructed and arranged to retain the suture lock in the body. The retainer is constructed and arranged to release the suture lock in response to a predetermined force being applied directly to the retainer by the suture lock ring.

In a further illustrative embodiment of the invention, a suture lock fastening device comprises an actuation handle and a fastening head operatively coupled to the actuation handle. The fastening head includes a body that has a chamber adapted to support at least a portion of a suture lock therein, and a cutter with a cutting edge that is constructed and arranged to cut a suture. The cutter is movably supported within the chamber of the body.

In another illustrative embodiment of the invention, a method of fastening a suture lock to secure a suture is provided. The method comprises acts of (a) threading a suture through a suture lock fastening device that includes a suture lock supported therein; (b) maintaining the suture lock in the suture lock fastening device with an irreversibly deformable retainer; (c) cinching the suture with the suture lock; and (d) deforming the retainer to release the suture lock from the suture lock fastening device.

In a further illustrative embodiment of the invention, a suture lock fastening device comprises an actuation handle, a fastening head operatively coupled to the actuation handle, a suture threader and a detachable handle. The fastening head is constructed and arranged to support and fasten a suture lock. The suture threader extends through the fastening head and is constructed and arranged to draw a suture through the fastening head. The detachable handle is constructed and arranged to support the fastening head as the suture is drawn through the fastening head with the suture threader.

BRIEF DESCRIPTION OF DRAWINGS

Various embodiments of the invention will now be described, by way of example, with reference to the accompanying drawings, in which.

DETAILED DESCRIPTION OF INVENTION

Figure 1:
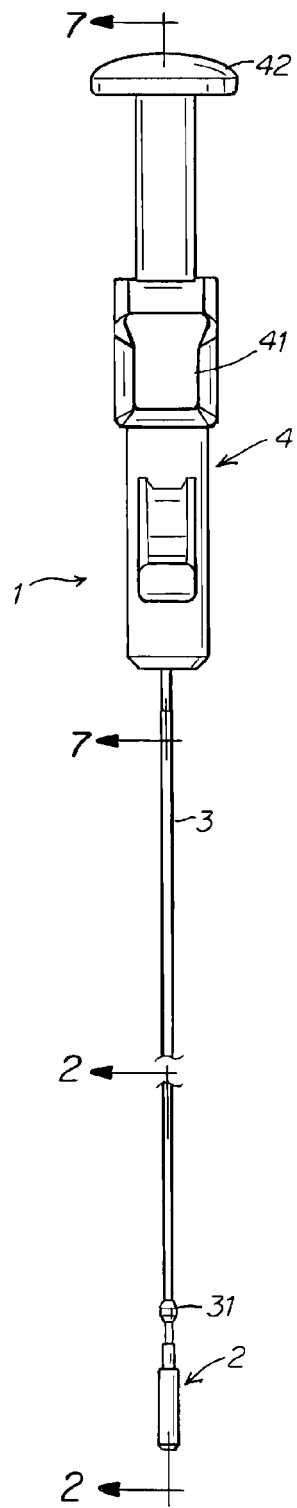
FIG. 1 is a side view of a suture lock fastening device according to one illustrative embodiment.

The present invention is directed to a suture lock fastening device that facilitates the fastening of a suture lock. The fastening device may be configured for endoscopic delivery of the suture lock to a surgical site within a patient. The fastening device may have an elongated, slender configuration that is insertable through a working or biopsy port of an endoscope.

Illustrative embodiments of the suture lock fastening device may include a fastening head at a distal end thereof that is operatively coupled to an actuation handle at a proximal end thereof. Operation of the handle actuates the fastening head so as to fasten the suture lock onto a suture and thereby cinch or lock the suture. The fastening head may also sever the suture proximate to the suture lock The fastening head may be configured to support a suture lock therein. In one embodiment, the fastening head may be configured to support a suture lock ring and a suture lock plug that is insertable into the ring to cinch or secure a suture therebetween. The suture lock ring and the suture lock plug may be supported in a longitudinal or axial arrangement. The handle may impart axial movement to the fastening head to drive the suture lock plug and the suture lock ring together.

In one aspect of the present invention, at least a portion of the fastening device may be configured to irreversibly deform in response to a predetermined force to release the suture lock from the fastening device. A fastening device with such a configuration may therefore be suitable as a single use device. However, it is to be appreciated that an irreversibly deformable configuration is not required for each embodiment of the fastening device.

The fastening head may include a retainer to maintain the suture lock within the fastening head for delivery to a desired location for securing a suture. The retainer may also be configured to restrain against forces that are applied to the suture lock by the fastening device to lock the suture lock on the suture. When the suture lock is fastened to the suture, the retainer may release the suture lock from the fastening head.

In one embodiment, the retainer may be configured to be irreversibly deformed to allow release of the suture lock from the fastening head when the retainer is subjected to a predetermined release force. In one embodiment, the retainer may include a deformable sleeve that irreversibly expands or stretches to release the suture lock from the fastening head. The sleeve may be fabricated from a polymer tube, such as a shrink tube. However, it is to be appreciated that an irreversibly deformable retainer is not required for each embodiment of the fastening device.

In another aspect of the present invention, the fastening device may be configured to release the suture lock in response to a force being applied to the retainer by the suture lock. In one embodiment, the retainer may be configured to release the suture lock in response to a predetermined force being applied directly to the retainer by a suture lock ring. However, it is to be appreciated that actuation of the retainer by the suture lock is not required for each embodiment of the fastening device.

In another aspect of the present invention, the fastening device may include a cutter that is movably supported within the fastening head to sever a suture. In one embodiment, the cutter may be movable in an axial direction to cut the suture. The cutter may be actuated by movement of a driver that is also used to fasten the suture lock within the fastening head. The fastening device may be configured so that the actuation of the cutter occurs after the driver initiates insertion of the suture lock plug into the suture lock ring. In this way, the suture will be cut only after the suture is secured by the suture lock. However, it is to be appreciated that a movable cutter is not required for each embodiment of the fastening device.

In another aspect of the present invention, a suture threader may be provided to facilitate the process of loading a suture through the fastening device and the suture lock. In one embodiment, the suture threader may be preloaded on the fastening device in such a manner as to facilitate proper positioning of a suture in the fastening device. The suture threader may include a detachable handle or grip that is mounted to the distal portion of the fastening device and allows a user to more easily grip the fastening device to load the suture into the fastening head. However, it is to be appreciated that a suture threader is not required for each embodiment of the fastening device.

Although described for use with an endoscope, it is to be appreciated that the suture lock fastening device may be configured for use with other medical instruments that may benefit from a suture lock fastening device. It is also to be appreciated that the suture lock fastening device may be employed as a stand alone device to secure a suture without the use of an endoscope or like instrument.

In one illustrative embodiment shown in FIG. 1, a suture lock fastening device 1 includes a fastening head 2, a shaft 3, and an actuation handle 4. The proximal end of the fastening device or any of its components refers to the part that is in the direction of the handle 4. The distal end of the fastening device or any of its components is the part that is in the direction of the fastening head 2. Axial or longitudinal movement refers to movement from the proximal end to the distal end or vice versa.

The fastening head 2 is operatively coupled to the actuation handle 4 via the shaft 3. Operation of the handle 4 actuates the fastening head 2 so as to fasten a suture lock onto a suture and thereby cinch or lock the suture.

Figure 2:
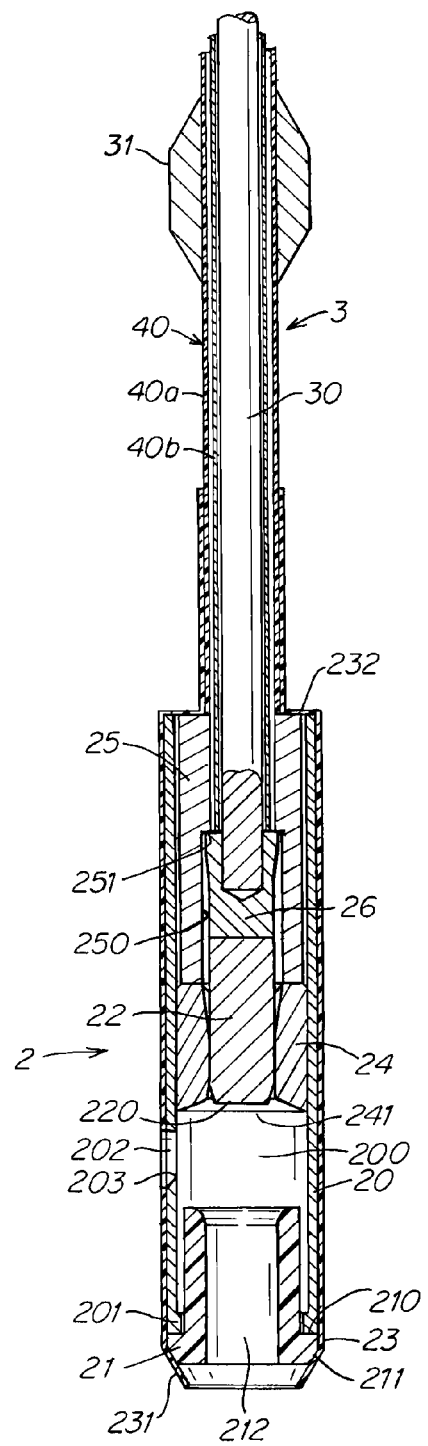
FIG. 2 is a cross-sectional view of a distal end of the suture lock fastening device taken along section line 2-2 of FIG. 1 shown with loaded suture lock components.

In one illustrative embodiment shown in FIG. 2, the fastening head 2 includes a body 20 that is configured to support a suture lock that may include a suture lock ring 21 and a suture lock plug 22. A retainer 23 is supported at a distal end of the body to maintain the suture lock within the fastening head as the suture lock is fastened to secure a suture. A cutter 24 is movably supported within the body to sever the suture. A driver 26 is movably supported within the body to drive the suture lock plug 22 into the suture lock ring 21 to cinch the suture.

The body 20 may be configured to have a substantially cylindrical shape with a chamber 200 for receiving the suture lock components 21, 22, the cutter 24 and the driver 26. In one embodiment, the body 20 includes a lip 201 at its distal end that extends radially inward toward the center of the body 20. The lip 201 may be configured to act as a stop to maintain the fastening head components within the body after the suture lock has been deployed from the fastening head 2.

The body 20 may be provided with a suture opening 202 along at least a portion of the body wall to allow passage of a suture therethrough. The suture opening 202 may be configured to permit at least a single suture strand to pass through without substantially compressing or stressing the suture. In one illustrative embodiment, the suture opening 202 is configured as a slot that is dimensioned to permit several strands of suture to pass through without substantially compressing or stressing the suture.

As shown in FIG. 2, the suture lock ring 21 may include a distal portion that is configured to protrude from the distal end of the body 20 when the ring is loaded into the fastening head. In one illustrative embodiment, the retainer 23 is configured to extend across at least a portion of a distal end of the suture lock ring to maintain the ring within the fastening head 2. In this manner, the retainer 23 holds the suture lock ring 21 in the body 20 of the fastening head 2 as the suture lock plug 22 is being inserted into the ring 21 during the fastening operation.

The retainer 23 may configured to release the suture lock from the fastening head 2 upon application of a predetermined release force. In one illustrative embodiment, the retainer 23 is configured to irreversibly deform in response to the release force to a deformed configuration that permits deployment of the suture lock from the fastening head 2. When the retainer has been irreversibly deformed upon release of the suture lock, the retention capability of the retainer has been substantially reduced so that the deformed retainer is no longer capable of providing adequate retention force that would allow another suture lock to be secured onto a suture. Irreversible deformation of the retainer may involve, but is not limited to, expanding, stretching, tearing, rupturing and/or shearing of the retainer.

The retainer may be configured to release the suture lock in response to the application of a release force against the retainer by the suture lock ring. In the illustrative embodiment shown in FIG. 2, the retainer 23 engages and holds the suture lock ring 21 in the distal end of the body 20. When the suture lock pin 22 has been fully mated with the suture lock ring 21, continued axial force applied to the suture lock is transmitted to the retainer 23 through the suture lock ring until the retainer is actuated to release the suture lock.

Various factors that may be considered in determining the retention and release forces of the retainer include, but are not limited to, the force required to insert the plug 22 into the ring 21 to secure a suture and the force that can be readily and comfortably generated by a person's hand to release the suture lock from the fastening head. If the release force of the retainer is too low, the plug 22 and ring 21 may not adequately secure the suture 50 before the lock is released from the body 20. However, if the release force is too high, it may be difficult for a user to release the suture lock from the fastening head 2.

In one embodiment, the retainer 23 is configured to have a release force of approximately 8 to 15 lbs. In another embodiment, the retainer is configured to have a release force of approximately 10 to 12 lbs. However, it is to be appreciated that the retainer may be configured to provide any desirable retention and/or release forces as would be apparent to one of skill in the art.

The retention and release forces of the retainer 23 may be affected by one or more factors that may include, but are not limited to, material properties, material thickness, and/or the structural characteristics of the retainer. The retainer 23 may be formed of a material that provides various characteristics including, but not limited to, strength, elasticity, conformability, biological inertness and/or lubricity.

In one embodiment, the retainer 23 formed of a polymer material, such as polyester, having a thickness of approximately 0.002 inches. It is to be appreciated, however, that the retainer may be formed from other suitable materials, including polymers, elastomers, metals, or combinations thereof, as would be apparent to one of skill in the art.

In one illustrative embodiment, the retainer 23 has a sleeve or tubular configuration that is configured to substantially cover the body 20. An opening 230 may be aligned with the suture slot 202 in the body 20 to provide for egress of a suture 50.

As shown, the retainer 23 may have a length that is greater than the body 20 with a portion of the retainer 23 extending beyond the distal end of the body 20 to form a lip or flange-like structure 231 that overlies and engages the distal end of suture lock ring 21. The lip 231 retains the ring 21 within the body 20 and prevents premature deployment of the suture lock from the fastening head 2.

As shown, a portion of the retainer 23 may also extend beyond the proximal end of the body 20 to form a proximal lip or flange-like structure 232 that overlies and engages the proximal end of the body to thereby secure the retainer 23 to the body 20. The proximal lip 232 retards axial movement of the retainer across the body when the distal portion 231 of the retainer subjected to forces applied through the suture lock ring. This arrangement ensures that the retainer 23 will maintain the suture lock within the fastening head during the fastening process.

In one embodiment, the retainer 23 is configured to closely conform to the shape of the underlying components, including the body 20 and the suture lock ring 21. The retainer 23 may be formed from a shrink tube or sleeve that shrinks about and conforms to the body upon the application of heat or by using another suitable process. In one embodiment, the retainer employs a polyester shrink tube having a wall thickness of approximately 0.002 inches, as available from Advanced Polymerics Inc. However, it is to be appreciated that other suitable shrink tubes may be used as would be apparent to one of skill in the art.

It is to be appreciated that the retainer may employ other irreversibly deformable configurations for retaining the suture lock as it is being secured to a suture and then releasing the suture lock after it is secured to the suture.

Figure 3:
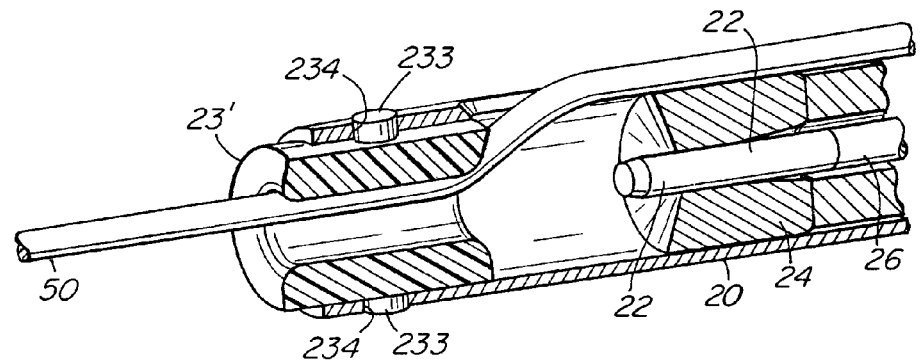
FIG. 3 is a cross-sectional perspective view similar to FIG. 2 of a suture lock fastening device according to another illustrative embodiment.

In another illustrative embodiment shown in FIG. 3, the retainer 23' includes a retention pin 233 that couples the suture lock ring 21 to the body 20. The retention pin 233 acts to prevent the suture lock ring 21 from moving axially with respect to the body 20. The pin 233 protrudes through and cooperates with a corresponding retention hole 234 in the wall of the body 20. The retention pin 233 may extend entirely through the retention hole 234 to reduce the potential for the pin to be inadvertently released from the body 20.

Figure 6:
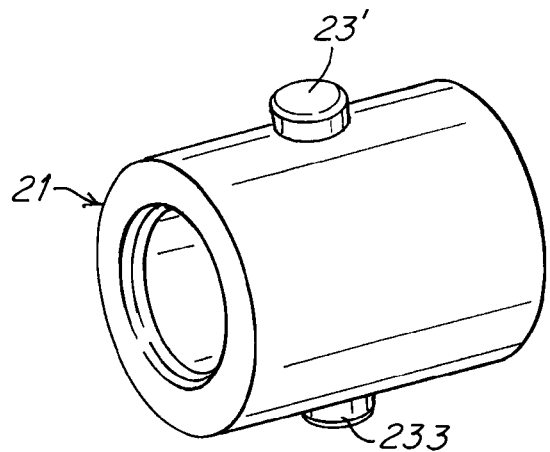
FIG. 6 is a perspective view of a suture lock ring and a suture lock retainer for use with the suture lock fastening device of FIG. 3.

In one illustrative embodiment shown in FIG. 6, the retention pin 233 is formed as an integral part of the ring 21. However, it is to be appreciated that the pin may be a separate component that interlocks the ring 21 to the body 20.

Figure 4:
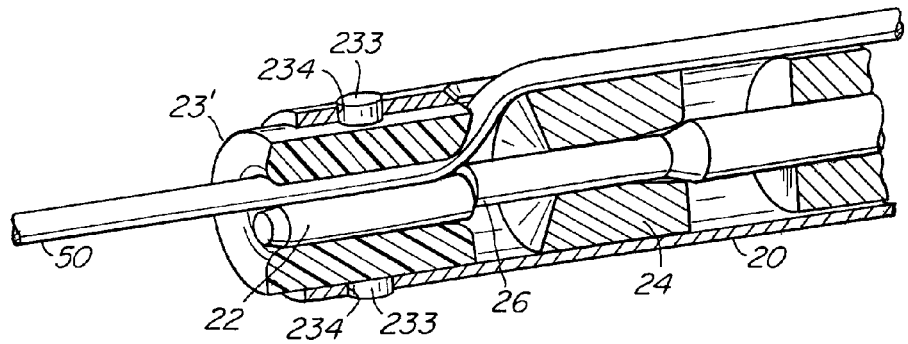
FIGS. 4-5 illustrate the suture lock fastening device of FIG. 3 in various stages of operation.
Figure 5:
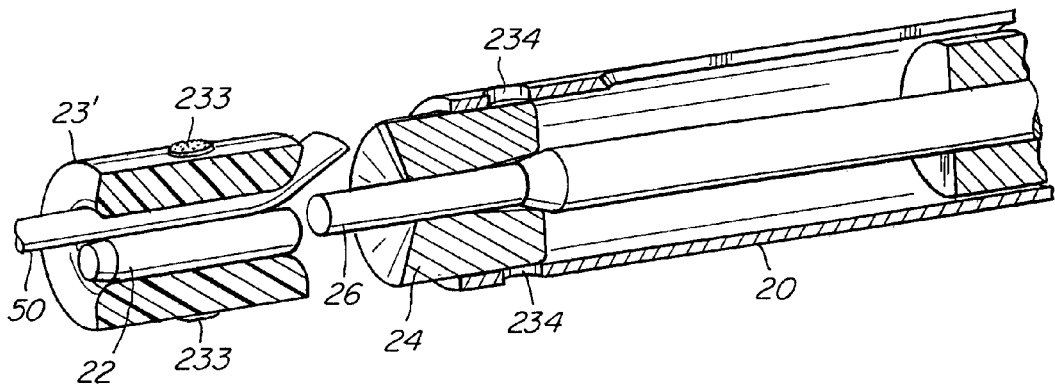

In one illustrative embodiment shown in FIGS. 3-5, the pin 233 may be configured to deform at a predetermined release force. In one embodiment, a portion of the pin 233 may be sheared off or otherwise deform to release the ring 21 from the fastening head 2 when the ring 21 is subjected to the release force. The pin 233 may be configured to shear or deform at a predetermined location.

In other alternative embodiments, the body 20 and/or the retainer 23 may be configured to tear or rupture to release the suture lock. For example, the body 20 may be configured with a tear or rupture zone that is located distal to the pin 233 so that the pin 233 tears through the body 20 when the ring 21 is subjected to the release force. Other configurations which require an irreversible deformation of the fastening device to release a suture lock from the fastening device could additionally or alternatively be used.

As described above, the fastening head 2 may also include a cutter 24 to sever the suture. In one illustrative embodiment shown in FIG. 2, the cutter 24 is supported for axial movement within the chamber 200 of the body 20. As shown, the cutter 24 may have an outer diameter that corresponds closely to the inner diameter of the body 20 to maintain axial alignment of the cutter with the suture lock components while allowing axial movement of the cutter within the body.

In the illustrative embodiment, the cutter 24 includes a sharp cutting surface or edge 241 along the outer distal edge of the cutter. As shown, the cutting edge 241 may extend around the entire outer diameter of the cutter 24. However, it is to be appreciated that the cutting edge 241 does not need to extend around the entire outer perimeter of the cutter 24 and may be limited to a portion of the cutter that severs the suture. For example, the sharp cutting surface 241 may extend only around the portion of the cutter 24 aligned with the suture slot 202 in the body 20.

Figure 8:
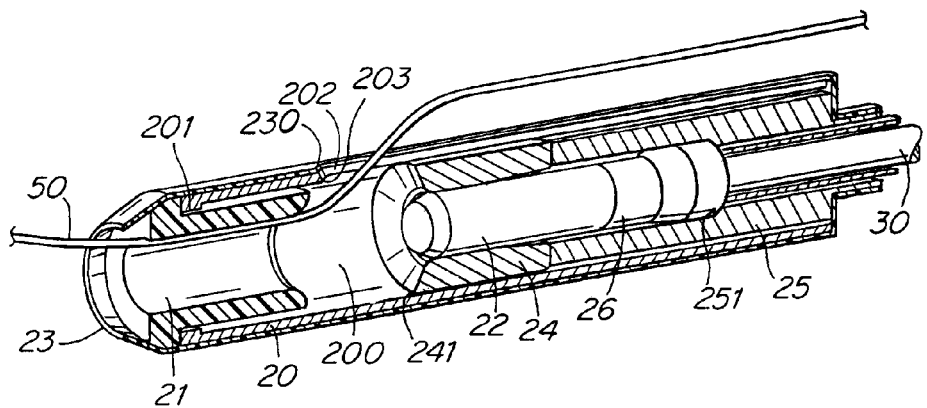
FIGS. 8-12 illustrate the suture lock fastening device of FIG. 2 in various stages of operation.
Figure 10:
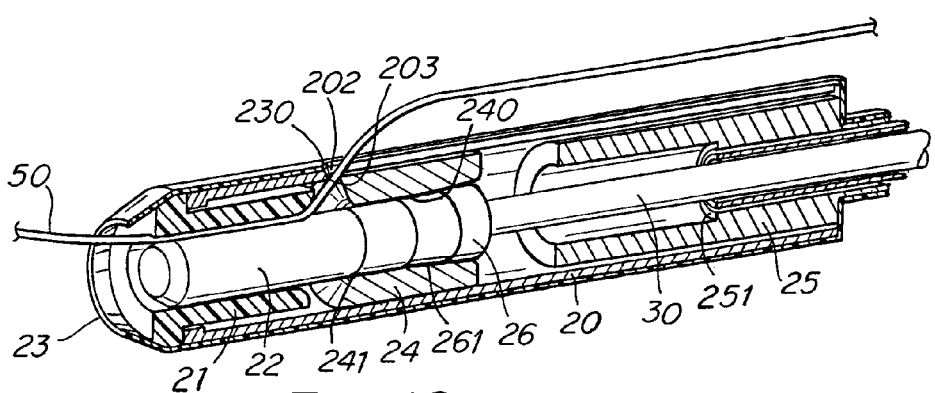

In one illustrative embodiment as shown in FIG. 8, the suture slot 202 may also include a sharp edge 203 on its distal inner edge which may be configured for use in conjunction with the cutter 24 to sever a portion of the suture extending through the slot. When the cutter 24 is moved distally and approaches the cutting edge 203 of the suture slot 202, a segment of the suture 50 positioned between the cutting edges of the cutter 24 and the suture opening is severed as shown in FIG. 10.

The cutter 24 may be configured to movably support the suture lock plug. In one illustrative embodiment shown in FIG. 2, the cutter 24 includes a center bore 240 that extends axially therethrough. The cutter is configured to slidably receive the suture lock plug 22 within the bore for axial movement relative to the cutter. The bore may have an inner diameter that corresponds closely to the outer diameter of the plug 22 to maintain axial alignment of the plug with the cutter and the ring while allowing axial movement of the plug along the cutter.

Figure 2A:
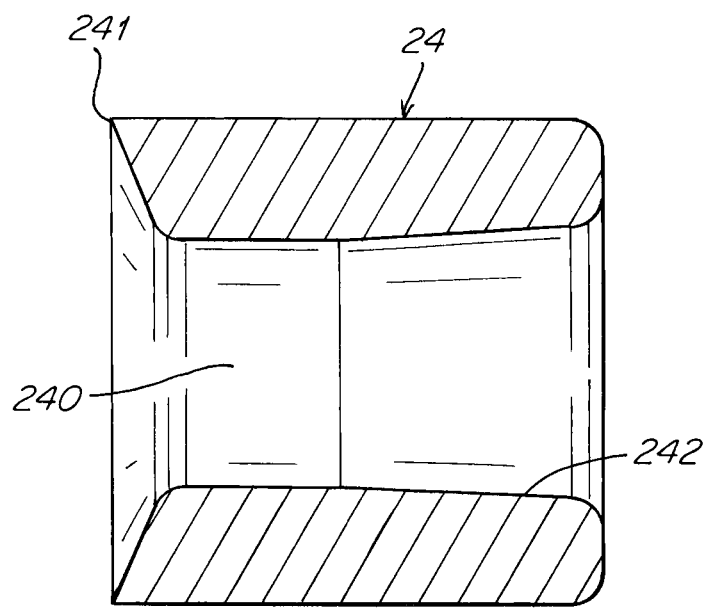
FIG. 2A is an enlarged view of the cutter of the suture lock fastening device of FIG. 2.

It may be desirable to actuate the cutter 24 only after the plug 22 has been at least partially driven from the cutter bore and into the ring. In one illustrative embodiment shown in FIG. 2A, a proximal portion 242 of the bore 240 may have a tapered configuration that decreases in the axial direction from the proximal end toward the distal end of the cutter 24. The tapered portion 242 of the bore provides a way to axially move the cutter 24 only when desired. For example, the cutter 24 may be designed to move axially only after the plug 22 supported therein has been displaced a predetermined distance.

In one illustrative embodiment to move the plug 22 without moving the cutter 24 in response to an axial force applied to the plug, the frictional force between the cutter 24 and body 20 may be greater than the frictional force between the cutter 24 and the plug 22. For example, the relatively low frictional force between the plug 22 and the cutter 24 may be created with a relatively loose fit between the components and/or employing materials having relatively low frictional properties. However it is accomplished, a larger frictional force between the cutter 24 and the body 20 will result in moving the plug 22 with respect to the cutter 24 in response to an axial force without also moving the cutter 24 within the body 20.

Other configurations for moving the plug 22 before the cutter 24 as a result of application of an axial force to the plug may additionally or alternatively be used. For example, an adhesive or a fixation device, such as a pin, a lip, or a detent, may be used to retard movement of the cutter 24 relative to the body 20.

In one embodiment, the cutter 24 is formed from 304 stainless steel. However, it is to be appreciated that the cutter may be formed from other suitable materials, such as metals, polymers, and combinations thereof. For example, the cutting edge 241 may be formed of a metal, while the remainder of the cutter may be formed from a different material, such as a plastic material.

Figure 2B:
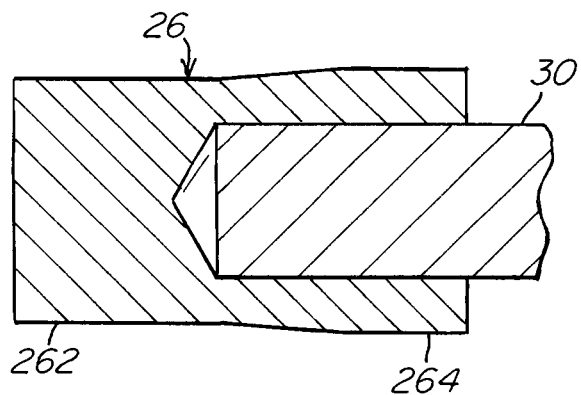
FIG. 2B is an enlarged view of the driver head of the suture lock fastening device of FIG. 2.

As shown in FIG. 2, the driver 26 is supported in the body 20 proximal to cutter 24 and the suture lock components. In one illustrative embodiment shown in FIG. 2B, the driver 26 includes a driver head with a distal portion 262 that is configured to engage and drive the suture lock plug 22 from the cutter 24 and into the suture lock ring 21 and a proximal portion 264 that is configured to engage and drive the cutter 24. The distal portion 262 may have a solid cylindrical shape of approximately the same diameter as the plug 22 so that the driver can distribute forces across the end of the plug while being driven through the cutter. The proximal portion 264 may have a tapered shape that corresponds to the tapered portion 242 of the bore 240 of the cutter 24. It is to be understood, however, that the driver 26 may employ other suitable configurations as would be apparent to one of skill in the art.

In the illustrative embodiment, the driver 26 is coupled to the actuation handle 4 via a drive wire 30 which extends along and is a component of the shaft 3. The drive wire 30 transfers movement of the actuation handle 4 to the fastening head 2. As shown, a distal end of the drive wire 30 mates with a counterbore in the proximal end of the driver 26.

The drive wire 30 may be configured to withstand compressive axial force without significant deformation yet be relatively flexible so that the fastening device may be flexed as necessary. In one embodiment, the drive wire 30 is formed of a flexible stainless steel wire. However, it is to be appreciated that other suitable materials may be used for the drive wire as would be apparent to one of skill in the art. It is also to be understood that the drive wire need not be flexible and may be a relatively rigid structure, for example, if a rigid fastening device is desired.

In the illustrative embodiment shown in FIG. 2, the fastening head 2 includes a sleeve adapter 25 that is supported at the proximal end of the body 20. The sleeve adapter 25 is substantially cylindrical and has a central bore 250 that supports the driver 26 in axial alignment with the plug 22 and the cutter 24. The proximal end of the bore 250 forms an abutment or stop 251 that engages the proximal end of the driver 26 to prevent the driver 26 from being retracted proximally out of the fastening head 2.

As shown, the outer diameter of the sleeve adapter 25 corresponds closely to the inner diameter of the body 20. The sleeve adapter 25 may be fastened or adhered to the body 20 so that the sleeve adapter 25 cannot move axially relative to the body 20. In another embodiment, the sleeve adapter 25 is integrally formed with the body 20 as a single piece.

In one illustrative embodiment, the sleeve adapter 25 is formed from 304 stainless steel. However, it is to be appreciated that the sleeve adapter may be formed from other suitable materials as would be apparent to one of skill in the art.

In one illustrative embodiment, as indicated above, the suture lock includes a suture lock ring 21 and a suture lock plug 22 that is insertable into the ring to cinch a suture therebetween. The ring and plug are supported by the body and may be preloaded into the fastening head 2.

As shown in FIG. 2, the ring 21 may have a substantially cylindrical shape with a center bore extending axially therethrough. In the illustrative embodiment, the ring includes a proximal portion that is configured to be inserted into the distal end of the body and an enlarged distal portion that is configured to protrude from the distal end of the body. The distal portion of the ring forms a lip 210 that engages the distal end of the body to prevent the ring 21 from being pushed back into the fastening head 2. The distal portion may include a tapered outer face 211 to facilitate distal movement of the ring 21 which may help eject the suture lock from the fastening head 2. It is to be appreciated that the ring may employ other suitable configurations as would be apparent to one of skill in the art.

As shown in FIG. 2, the suture lock plug 22 may have a substantially cylindrical shape that is configured to be inserted into the ring. In the illustrative embodiment, the plug 22 includes a tapered distal end 220 to facilitate insertion of the plug 22 into the bore 212 of the ring 21. It is to be appreciated that the plug may have other suitable configurations as would be apparent to one of skill in the art.

The ring 21 and plug 22 may be formed from any suitable material, including metals, polymers or plastics. In one embodiment, the ring 21 and the plug 22 are formed from a polymer, such a polyetheretherketone (PEEK). However, it is to be understood the ring and the plug may be formed from other suitable materials apparent to one of skill in the art.

In one illustrative embodiment, the shaft 3 includes a sleeve 40 with an inner passage through which extends the drive wire 30. The sleeve 40 connects the fastening head 2 to the actuation handle 4 in a manner that permits axial movement of the drive wire 30 therethrough to actuate the fastening head. As shown, the sleeve 40 includes an outer sleeve 40a and an inner sleeve 40b concentrically disposed within the outer sleeve.

The inner and outer sleeves provide the shaft with one or more desirable properties or characteristics. For example, the outer sleeve 40a may provide the shaft 3 with lubricity and the inner sleeve 40b may provide the shaft 3 with strength and flexibility. In one embodiment, the outer sleeve 40a is formed from a polymer or elastomer, such as PEBAX, and the inner sleeve 40b is formed form a stainless steel hypotube. However, it is to be appreciated that the sleeves may be formed of other suitable materials as would be apparent to one of skill in the art.

The shaft 3 may have any length suitable for the intended application for the fastening device 1. In one illustrative embodiment for use in endoscopic bariatric surgery, the shaft 3 should have sufficient length that is capable of extending from outside the patient to desired regions of a patient's stomach.

For some applications of the fastening device 1, it may be desirable to precisely position the fastening head 2 relative to an endoscope or other surgical tool. In one illustrative embodiment shown in FIG. 2, the fastening device 1 includes a positioning sleeve 31 that is configured to engage a corresponding feature of an endoscope to position the fastening head 2 at a desired location relative to the endoscope. The positioning sleeve 31 may have any shape or configuration that is suitable to engage the corresponding feature on the endoscope or other instrument employed during the surgical procedure.

Figure 7:
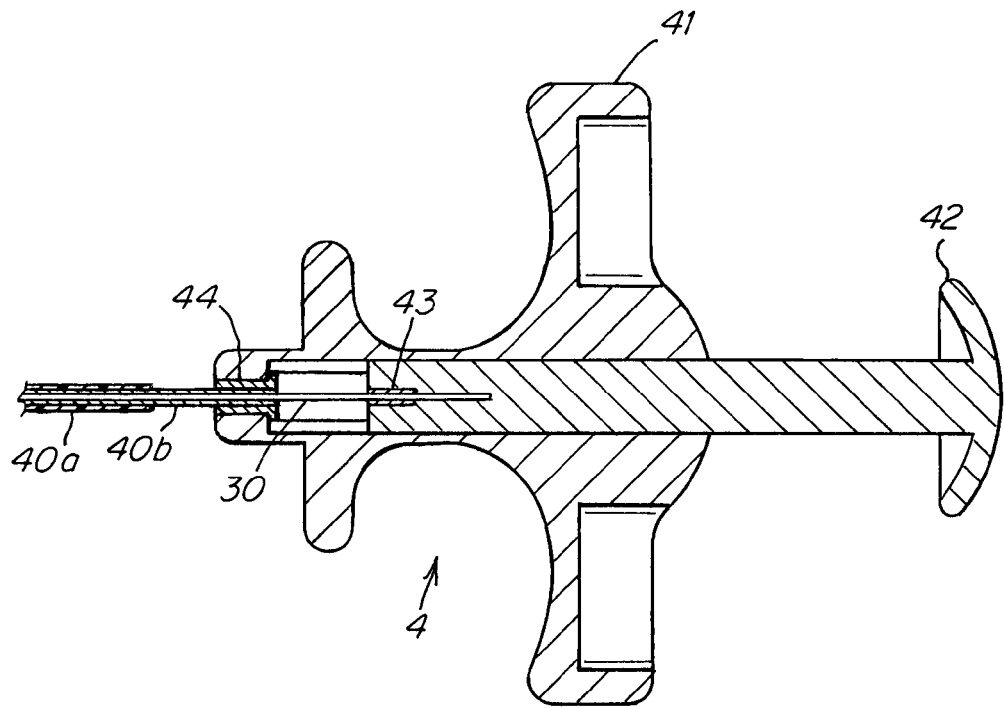
FIG. 7 is a cross-sectional view of the actuation handle of the suture lock fastening device taken along section line 7-7 of FIG. 1.

In one illustrative embodiment shown in FIG. 7, the actuation handle 4 includes a grip 41 and an actuator 42 that is movably supported on the grip. The actuator 42 is coupled to the drive wire 30 so that axial movement of the actuator 42 causes corresponding movement of the drive wire 30. As described above, axial movement of the drive wire in the distal direction actuates driver 26 within the fastening head 2 to fasten and release the suture lock.

Although the grip 41 and actuator 42 are shown to have a particular configuration, it is to be appreciated that the grip 41 and the actuator 42 may have any suitable configuration that allows a user to grasp the fastening device 1 and actuate the actuator 42 relative to the grip 41. For example, the grip 41 may be configured to be easily held by a user and allow a user to counteract a force placed on the actuator 42. In one embodiment, the grip has a T-handle configuration and the actuator is configured as a plunger with a rounded head at its proximal end. However, it is to be appreciated that the grip and the actuator may employ other suitable configurations as would be apparent to one of skill in the art.

In the illustrative embodiment shown in FIG. 7, the drive wire 30 and the sleeve 40 may be secured to the handle using various insert supports. The drive wire 30 is attached to the distal end of the actuator 42 using a drive wire support 43 that acts as a bushing to maintain the drive wire centered in the actuator and reduces the potential for the drive wire to buckle. The inner sleeve 40b is attached to the grip 41 using a handle insert 44 that acts as an interface between the metal hypotube and the relatively softer plastic material which may be used to form the handle. It is to be appreciated that other connection arrangements may be employed to attach the handle to the various components of the fastening device as would be apparent to one of skill in the art.

In the illustrative embodiments above, various components of the fastening device 1 have been described as having cylindrical shapes with cylindrical inner bores. However, it is to be understood that the components may employ other shapes, either externally or internally. For example, if it is desirable to prevent rotation of selected components with respect to each other, the bore of one component, such as the body 20, could be non-circular (e.g., ellipsoid or polygonal) and the outer surfaces of other components, such as the sleeve adapter 25, the driver head 26, the cutter 24 and/or suture lock ring 21 could have a corresponding non-circular cross sectional shape. Similarly, the suture lock plug 22 could have a non-circular cross sectional shape and the inner bore of the cutter 24 and the suture lock ring 21 could have a corresponding non-circular cross sectional shape.

In the illustrative embodiment above, various components of the fastening device 1 and the suture lock have been described as having tapered shapes. It is to be appreciated that other suitable interfaces between components may additionally or alternatively be used as would be apparent to one of skill in the art.

One illustrative embodiment of fastening a suture lock with the suture lock fastening device is described below in conjunction with FIGS. 8-12. In use, a surgical procedure may be performed on a patient using a suturing instrument, such as an endoscopic suturing device as disclosed in U.S. Patent Application Publication US 2005/0033319, which is incorporated herein by reference. When one or more sutures have been placed in a desired location, the suturing instrument is removed from the patient so that the sutures may be secured with a suture lock.

In an initial position of the fastening head 2 as shown in FIG. 8, a suture 50 is threaded through the suture lock ring 21, the chamber 200 of the body and out through the suture slot 202. The suture lock plug 22 is supported within the body 20 by the cutter 24 and the sleeve adapter 25. As shown, the plug 22 is axially aligned with and spaced proximally to the suture lock ring 21. The cutter 24 is located proximal to the suture slot 202 so that there is adequate spacing between the cutting edge 241 of the cutter 24 and the cutting edge 203 of the slot to permit the suture 50 to exit the fastening head 2 through the suture slot 202.

The fastening head 2 of the fastening device is then advanced along the suture to the surgical site. The suture may be pulled taut to facilitate advancement of the fastening device. The fastening head 2 is advanced to its desired location, such as when the positioning sleeve 31, if employed, abuts a mating portion of the endoscope.

Figure 9:
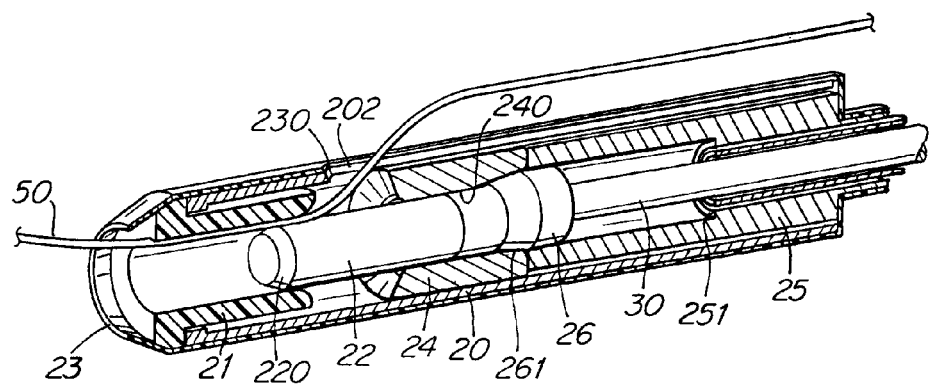

FIG. 9 illustrates an initial cinched position for the fastening head 2 in which the suture lock plug has been advanced distally through the cutter 24 and into the proximal end of the suture lock ring 20. This is accomplished by moving the actuator 42 distally relative to the grip 41, with the suture 50 pulled taut, which causes the drive wire 30 and the driver 26 to move distally against the plug 22 and drive the plug distally through the cutter 24. During this initial actuation, only the plug 22 is moved along the body by the driver 26 and the cutter 24 remains in its initial position. After the pin has been advanced a predetermined distance from the cutter 24 and into the proximal end of the ring 21 to initially capture the suture therebetween, the tapered surface 261 of the driver 26 engages the mating tapered bore 240 of the cutter 24 to initiate distal movement of the cutter 24.

FIG. 10 illustrates a final cinched position of the fastening head 2 in which the suture lock pin 21 has been fully advanced into the suture lock plug 20 to cinch the suture. During this segment of the fastening sequence, application of an axial force on the drive wire 30 causes the tapered surface 261 of the driver 26 to engage and drive the cutter 24 in the distal direction along the body 20 while continuing to drive the pin 22 into the plug 21. As the cutter is advanced distally, the cutting edge 241 of the cutter 24 and the cutting edge 203 of the body 20 eventually capture and sever the portion of the suture 50 extending through the suture slot 202.

Figure 11:
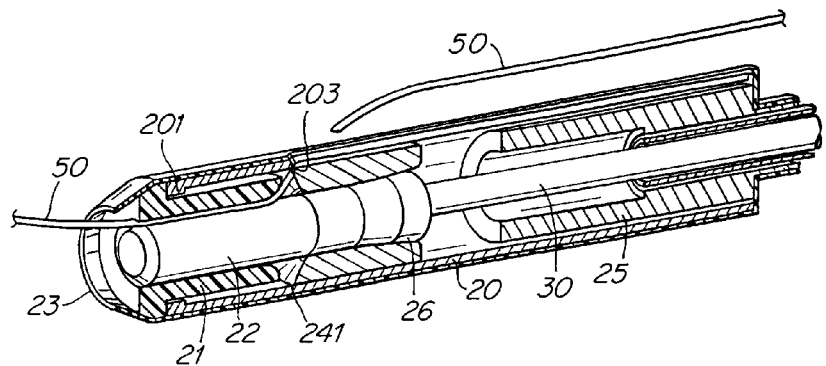

FIG. 11 illustrates a cut position of the fastening head 2 in which the suture 50 has been completely severed by the cutting edges 203, 241 proximal to the suture lock. The trailing end of the suture 50 may then be removed from the patient.

Figure 12:
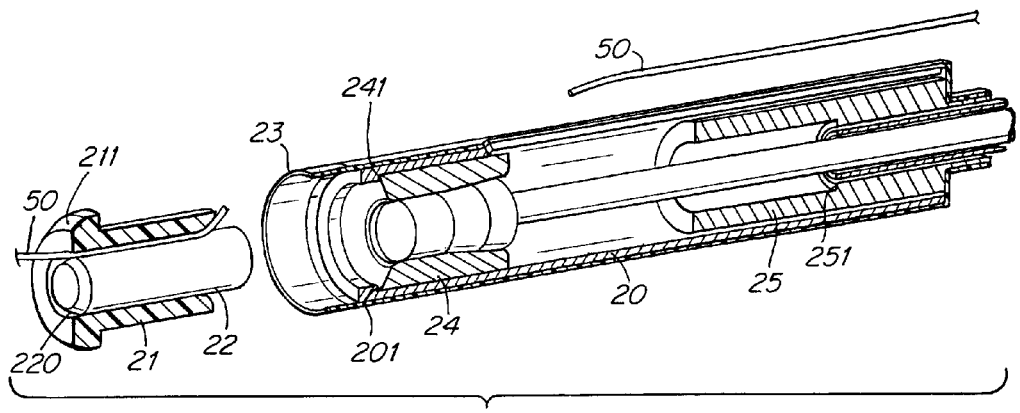

FIG. 12 illustrates a deployment position of the fastening head 2 in which the suture lock is deployed. This is accomplished by applying additional axial force on the actuator 42 which results in the suture lock ring 21 exerting a force against the retainer 23. When the force applied against the retainer 23 reaches a predetermined release force, the retainer 23 irreversibly deforms to allow passage of the cinched suture lock from the fastening head. The cutter 24 and the driver 26 are retained in the fastening head 2 by the distal lip 201 on the body 20.

To facilitate threading of a suture through the fastening head 2, it may be desirable to employ a suture threading arrangement that may be preloaded on the distal end of the fastening device 1.

Figure 13:
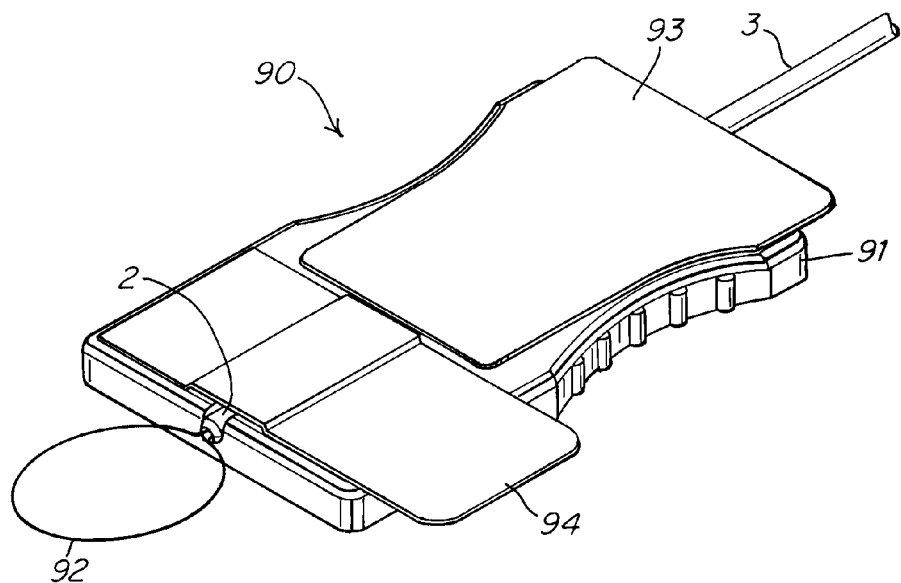
FIG. 13 is a perspective view of a distal portion of a suture lock fastening device with a suture threading device according to another illustrative embodiment.

In one illustrative embodiment shown in FIG. 13, a suture threading device 90 is provided with the suture lock fastening device to facilitate threading of a suture through the fastening head 2. The threading device includes a handle 91 and a suture threader 92. The handle 91 is configured to be grasped by a user to support the fastening head 2 as the suture is drawn through the fastening head with the suture threader 92.

The handle 91 may be detachably mounted to the fastening device 1 so that the handle may be readily removed to facilitate insertion of the fastening device into a patient once the suture has been threaded through the fastening head 2. In one embodiment, the handle may be configured to snap-fit onto the fastening head 2. It is to be appreciated, however, that other suitable attachment arrangement may be implemented with the handle.

In one embodiment, the suture threader 92 includes a threading loop that may act as a snare to capture the suture. The threader 92 extends in a distal direction through the suture slot 202 in the body 20, the suture lock plug 21 and the retainer 23 with the threading loop protruding from the distal end of the fastening head 2. The proximal ends of the suture threading loop are connected to a pull tab 93 that provides a grip for pulling the suture threader and the suture through the fastening head. In one embodiment, the threading loop may include a single loop of flexible wire or other flexible strong material as would be apparent to one of skill in the art.

Figure 17:
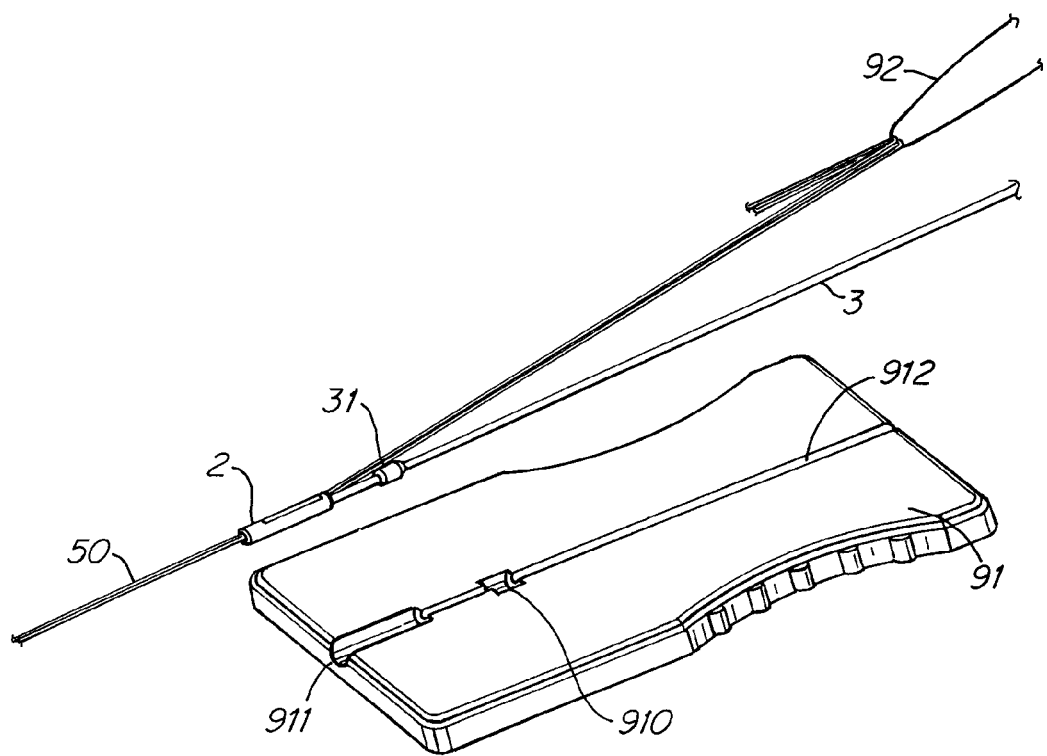

In one illustrative embodiment shown in FIG. 17, the handle 91 includes a base with an elongated channel 912 that is configured to receive the distal portion of the fastening device. The base also includes one or more cavities that are configured to mate with particular features or components of the fastening device. As shown, the base 91 may include a first cavity 910 for the holding the positioning sleeve 31 and a second cavity 911 for holding the fastening head 2. The proximal end of the second cavity forms an abutment or stop that is engaged by the proximal end of the fastening head 2 to counteract forces required to pull the suture threader through the fastening head. Supporting the distal end of the fastening device 1 in this manner may facilitate loading the suture.

As shown in FIG. 13, the suture threading device 90 may include a fastener, such as a securing tape 94, which helps maintain the distal end of the fastening device 2 within the handle 91. It is to be appreciate, however, that the securing tape may not be necessary and that other suitable fastening arrangements may be employed to retain the fastening head within the handle as would be apparent to one of skill in the art.

One illustrative embodiment of loading a suture into the fastening head 2 is described below in conjunction with FIGS. 14-17.

Figure 14:
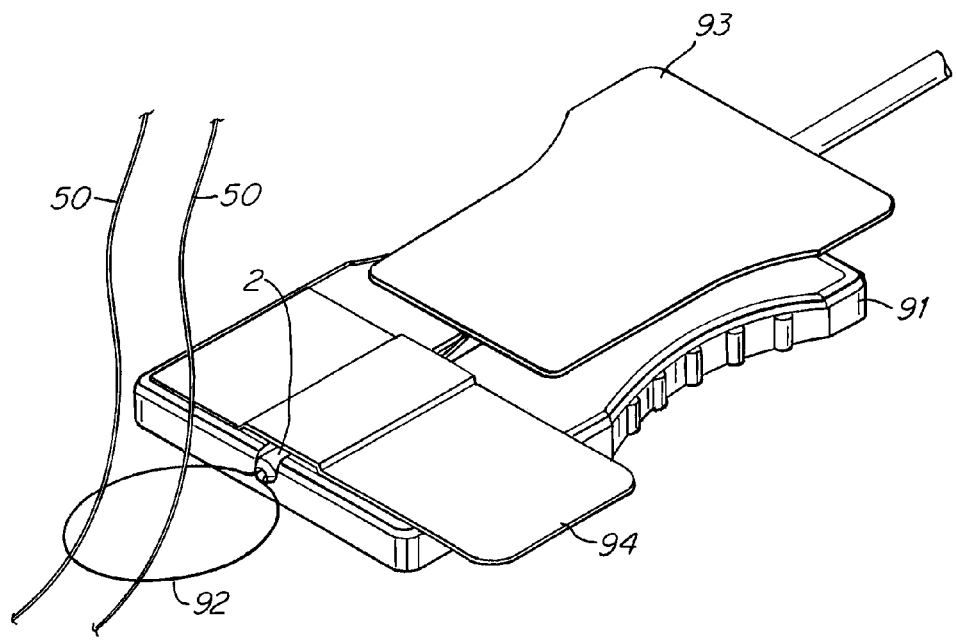
FIGS. 14-17 illustrate the suture threading device of FIG. 13 in various stages of threading a suture through the suture lock fastening device.
Figure 15:
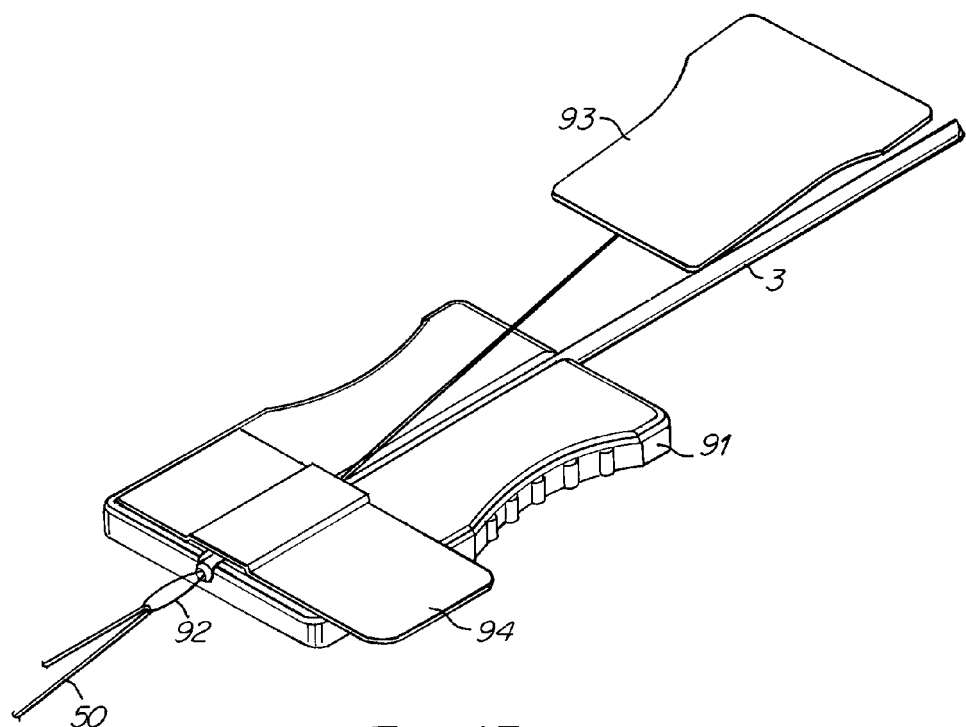
Figure 16:
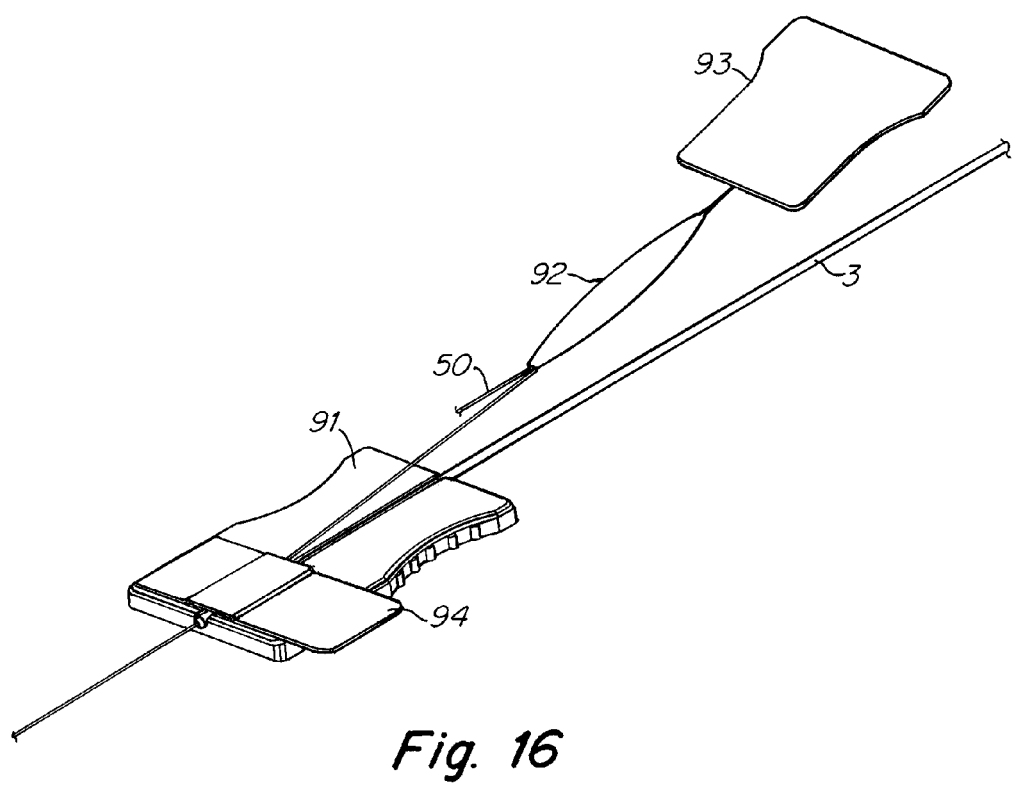

As shown in FIG. 14, a suture 50 is threaded through the suture threader 92. Once the suture 50 has been pulled through the threading loop, the pull tab 93 is pulled in the proximal direction relative to the fastening head 2 as shown in FIGS. 15 and 16. This action draws the threader loop and the suture 50 through the distal end of the fastening head and then out through the suture slot 202 in the side of the fastening head. Once the suture 50 has been fully threaded through the fastening head 2, the securing tape 94 may be removed, as shown in FIG. 17, and the handle may be detached from the distal portion of the fastening device. Thereafter, the fastening device may be advanced along the suture to the desired surgical site to secure the suture as described above.

Although the handle 91 may facilitate loading of a suture into the fastening device, it is to be appreciated that a handle is not required for each embodiment of the fastening device. If desired, the suture threader 92 may be used as a stand alone device to thread a suture through the fastening head as described above. Instead of grasping a handle, the user may directly grasp the distal portion of the fastening device as the suture is being pulled through the fastening head.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. A suture lock fastening device, comprising:
an actuation handle; and
a fastening head operatively coupled to the actuation handle, the fastening head including,
a body that is constructed and arranged to support a suture lock; and
a retainer that is constructed and arranged to retain at least a portion of the suture lock in the body, the retainer being constructed and arranged to be irreversibly deformed to release the suture lock from the fastening head, the retention capability of the retainer being substantially reduced when the retainer has been irreversibly deformed upon release of the suture lock so that the deformed retainer is no longer capable of providing adequate retention force that would allow a suture lock to be secured onto a suture.

2. The suture lock fastening device according to claim 1, wherein the retainer includes an irreversibly deformable sleeve.

3. The suture lock fastening device according to claim 2, wherein the sleeve includes a distal portion that extends beyond a distal end of the body to retain the portion of the suture lock in the body.

4. The suture lock fastening device according to claim 2, wherein the retainer includes a shrink tube sleeve.

5. The suture lock fastening device according to claim 4, wherein the shrink tube sleeve is constructed and arranged to be irreversibly stretched to release the suture lock from the body.

6. The suture lock fastening device according to claim 1, wherein the retainer includes an irreversibly deformable pin.

7. The suture lock fastening device according to claim 6, wherein the pin is constructed and arranged to break upon the application of a predetermined force to release the suture lock from the body.

8. The suture lock fastening device according to claim 7, wherein the retainer is constructed and arranged to release the suture lock in response to a predetermined force being applied directly to the retainer by the suture lock.

9. The suture lock fastening device according to claim 1, wherein the fastening head includes a cutter with a cutting edge that is constructed and arranged to cut a suture.

10. The suture lock fastening device according to claim 9, wherein the cutter is movably supported within the body.

11. The suture lock fastening device according to claim 10, wherein the cutter is constructed and arranged to support a portion of the suture lock.

12. The suture lock fastening device according to claim 9, wherein the fastening head includes a driver that is movably supported by the body to fasten the suture lock upon actuation of the actuation handle.

13. The suture lock fastening device according to claim 1, further comprising an elongated shaft operatively coupling the actuation handle to the fastening head.

14. The suture lock fastening device according to claim 13, wherein the shaft is flexible.

15. The suture lock fastening device according to claim 13, wherein the shaft includes at least one sleeve and a drive wire slidably supported by the sleeve, the drive wire constructed and arranged to actuate the fastening head upon actuation of the actuation handle.

16. A suture lock fastening device for fastening a suture lock, the suture lock including a suture lock ring and a suture lock plug that is insertable into the suture lock ring, the suture lock fastening device comprising:
an actuation handle; and
a fastening head operatively coupled to the actuation handle, the fastening head including,
a body that is constructed and arranged to support the suture lock ring and the suture lock plug;
a cutter with a cutting edge that is constructed and arranged to cut a suture; and
a retainer that is constructed and arranged to retain the suture lock in the body, the retainer being constructed and arranged to release the suture lock solely in response to a predetermined force being applied directly to the retainer by the suture lock ring.

17. The suture lock fastening device according to claim 16, wherein the retainer is constructed and arranged to be deformed upon application of the predetermined force to release the suture lock.

18. The suture lock fastening device according to claim 17, wherein the retainer is constructed and arranged to be irreversibly deformed to release the suture lock.

19. The suture lock fastening device according to claim 18, wherein the retainer includes a shrink tube sleeve with a distal portion that extends beyond a distal end of the body to engage the suture lock ring.

20. The suture lock fastening device according to claim 16, wherein the cutter is movably supported within the body.

21. The suture lock fastening device according to claim 20, wherein the cutter is constructed and arranged to support the suture lock plug.

22. The suture lock fastening device according to claim 16, wherein the fastening head includes a driver that is movably supported by the body to fasten the suture lock upon actuation of the actuation handle.

23. The suture lock fastening device according to claim 16, further comprising an elongated shaft operatively coupling the actuation handle to the fastening device.

24. The suture lock fastening device according to claim 23, wherein the shaft is flexible.

25. The suture lock fastening device according to claim 24, wherein the shaft includes at least one sleeve and a drive wire slidably supported by the sleeve, the drive wire constructed and arranged to actuate the fastening head upon actuation of the actuation handle.

* * * * *